(12) United States Patent
Di Croce et al.

(10) Patent No.: US 10,588,545 B2
(45) Date of Patent: Mar. 17, 2020

(54) MONITORING SYSTEM WITH PRESSURE SENSOR IN FLOOR COVERING

(71) Applicant: TARKETT GDL, Lentzweiler (LU)

(72) Inventors: Pascal Di Croce, Wiltz (LU); Christophe Reithler, Wiltz (LU)

(73) Assignee: TARKETT GDL, Lentzweiler (LU)

( * ) Notice: Subject to any disclaimer, the term of this patent is extended or adjusted under 35 U.S.C. 154(b) by 0 days.

(21) Appl. No.: 15/529,187

(22) PCT Filed: Nov. 23, 2015

(86) PCT No.: PCT/EP2015/077341
§ 371 (c)(1),
(2) Date: May 24, 2017

(87) PCT Pub. No.: WO2016/083294
PCT Pub. Date: Jun. 2, 2016

(65) Prior Publication Data
US 2017/0354350 A1 Dec. 14, 2017

(30) Foreign Application Priority Data
Nov. 24, 2014 (EP) ..................... 14194494

(51) Int. Cl.
*A61B 5/11* (2006.01)
*A61B 5/00* (2006.01)
*G08B 13/10* (2006.01)

(52) U.S. Cl.
CPC .......... *A61B 5/1117* (2013.01); *A61B 5/6889* (2013.01); *A61B 2562/046* (2013.01); *G08B 13/10* (2013.01)

(58) Field of Classification Search
CPC ....... A61B 5/11; A61B 5/1113; A61B 5/1115; A61B 5/1116; A61B 5/1117;
(Continued)

(56) References Cited

U.S. PATENT DOCUMENTS

| | | |
|---|---|---|
| 5,592,152 A | 1/1997 | Huang |
| 5,877,675 A | 3/1999 | Rebstock et al. |

(Continued)

FOREIGN PATENT DOCUMENTS

| | | |
|---|---|---|
| EP | 2263217 A1 | 12/2010 |
| WO | 0075417 A1 | 12/2000 |

OTHER PUBLICATIONS

International Search Report; International Application No. PCT/EP2015/077341; International Filing Date Nov. 23, 2015; dated Feb. 18, 2016; 4 pages.

(Continued)

*Primary Examiner* — Mohamed Barakat
(74) *Attorney, Agent, or Firm* — Cantor Colburn LLP

(57) ABSTRACT

A monitoring system comprises a floor covering with a sheet-type pressure sensor and a sensor control unit. The latter includes an ADC for providing a digital raw signal, a microcontroller configured to carry out data extraction by signal processing of the digital raw signal and generating a digital processed signal having a lower digital bandwidth than the digital raw signal, and a communications module connected to or integrated within the microcontroller so as to receive the digital processed signal. The communications module is configured to establish data communication with one or more database servers and to transmit the extracted data to the one or more database servers.

20 Claims, 6 Drawing Sheets

(58) Field of Classification Search
CPC ... A61B 5/1118; A61B 5/6889; A61B 5/6892; A61B 5/7465; A61B 5/747; A61B 2562/0247; A61B 2562/046; G08B 21/04–21/0438; G08B 21/0461; G08B 21/0469; G08B 21/0484; G08B 21/0492; H01L 25/16; H01L 27/20
See application file for complete search history.

(56) References Cited

U.S. PATENT DOCUMENTS

| | | |
|---|---|---|
| 6,515,586 B1 | 2/2003 | Wymore |
| 2006/0171570 A1* | 8/2006 | Brendley ............... G08B 13/10 382/115 |
| 2008/0097250 A1 | 4/2008 | Tochigi et al. |
| 2008/0117060 A1 | 5/2008 | Cuddihy et al. |
| 2008/0204258 A1* | 8/2008 | Dayton ............... F21V 23/0442 340/600 |
| 2009/0056465 A1* | 3/2009 | Nakamura ............... A61B 5/11 73/756 |
| 2010/0194525 A1 | 8/2010 | Do et al. |
| 2010/0224919 A1* | 9/2010 | Bauer ..................... G01L 1/005 257/295 |
| 2010/0231400 A1* | 9/2010 | Von Mohr ......... A47G 27/0225 340/665 |
| 2010/0253183 A1* | 10/2010 | Ando ....................... G01L 1/16 310/338 |
| 2011/0313714 A1* | 12/2011 | Lieberman ........... A61B 5/1036 702/139 |
| 2012/0151093 A1* | 6/2012 | Zheng ..................... G04G 7/02 709/248 |
| 2014/0215928 A1 | 8/2014 | Desgorces et al. |
| 2015/0054649 A1* | 2/2015 | Desgorces ......... G08B 21/0469 340/573.1 |
| 2015/0112722 A1* | 4/2015 | Dees .................... A61B 5/7275 705/3 |
| 2015/0123931 A1* | 5/2015 | Kitchens ............... G06F 3/0414 345/174 |
| 2015/0364059 A1* | 12/2015 | Marks ................ G09B 19/0038 482/9 |
| 2016/0320899 A1* | 11/2016 | Watazu ................... G06F 3/047 |
| 2017/0317269 A1* | 11/2017 | Zhang .................. H01L 41/047 |

OTHER PUBLICATIONS

Written Opinion of the International Searching Authority; International Application No. PCT/EP2015/077341; International Filing Date Nov. 23, 2015; dated Feb. 18, 2016; 5 pages.

* cited by examiner

MONITORING SYSTEM WITH PRESSURE SENSOR IN FLOOR COVERING

CROSS REFERENCE TO RELATED APPLICATIONS

This is a U.S. national stage of PCT International Application No. PCT/EP2015/077341, filed on 23 Nov. 2015. Priority under 35 U.S.C. § 119(a) and 35 U.S.C. § 365(b) is claimed from European Application No. 14194494.2 filed on 24 Nov. 2014, the disclosure of which is also incorporated herein by reference in its entirety.

FIELD OF THE INVENTION

The invention generally relates to a monitoring system, especially, but not exclusively, for monitoring persons in rooms of a caretaking institution, such as, e.g., a hospital, a nursing home or a retirement home, or a penal institution while preserving, as much as possible, the monitored persons' autonomy and privacy.

BACKGROUND OF THE INVENTION

Rooms in healthcare facilities are conventionally equipped with nurse call buttons (or other types of switches), enabling the persons in the rooms to request assistance from the nurses or caregivers. Pressing the call button triggers a signal to the caregivers' room and possibly to caregivers' pagers or other mobile devices. Such call systems are useful for responding to ad-hoc needs expressed by the room occupants having the button or the switch in reach. However, they are only partly appropriate in case of emergency, especially in the event of a fall.

There is, therefore, a need for monitoring systems, which allow, inter alia to give the alarm if a fall of the person who is taken care of is detected.

U.S. Pat. No. 5,877,675 discloses a portable, three-way wireless communication system that provides a patient with a direct link to a caregiver, as well as a central facility such as a nurse's station. The system is comprised of a patient unit, a caregiver unit and a central station. The patient unit is designed to be small and portable, and can be worn on the patient's wrist or the like. The unit permits a patient to send a request for assistance directly to an assigned caregiver, and provides for two-way voice communications between the patient and the caregiver. The unit stores information associated with the patient, such as identification, medications, attending physician, and the like. The caregiver unit is also portable, and provides two-way voice communications with patients and other caregivers. The unit displays information about each patient to whom the caregiver is assigned. The central station functions as a backup, in the event that a caregiver is not able to timely respond to a call from a patient. In addition, it stores more detailed information regarding patients, which can be accessed by the caregiver via their individual units.

US 2008/0117060 A1 discloses a system for facilitating independent living of individuals. The system, which is adapted to communicate with one or more caregivers, comprises a worn device fitted with a panic button and an activity sensor, sensors placed in the user's living area and an off-site monitoring center. A first subsystem monitors the activity levels of the individual and determines whether the activity level is indicative of a decline in the individual's health status; a second subsystem can be selectively activated by the individual to alert caregivers that assistance is needed; a third subsystem automatically alerts caregivers that assistance is needed based at least in part on determination of the first subsystem; and a fourth subsystem monitors whether the individual is exhibiting wandering activity.

Floor-mounted monitoring systems, are, as such, well known in various applications.

For instance, U.S. Pat. No. 5,592,152 relates to an intruder detecting device, which is to be installed in an integrated raised flooring system. The intruder detecting device includes a floor panel assembly and a plurality of pedestals for supporting the floor panel assembly on a base floor, a housing, a restoring member, a switch unit and a piston. The restoring member biases an upper housing part away from a lower housing part. The switch unit is mounted on the lower housing part and has a resilient switch contact which can be deactivated by the piston.

EP 2 263 217 discloses an object tracking system, comprising a dense sensor field in the floor. The object tracking system detects sensor activations and links an object to each activation. It further produces event information describing events for immediate or later use. The system detects events according the conditions defined for them, on the basis of sensor observations. The conditions can relate to the essence of the objects, e.g. to the strength of the observations linked to the object, to the size and/or shape of the object, to a temporal change of essence and to movement. The system can be used e.g. for detecting the falling, the getting out of bed, the arrival in a space or the exit from it of a person by tracking an object with the dense sensor field, and for producing event information about the treatment or safety of the person for delivering to the person providing care.

U.S. Pat. No. 8,138,882 discloses an electronic multi-touch floor covering that has numerous sensors arranged in a dense two-dimensional array to identify shapes. The electronic multi-touch floor covering identifies the shape of an object that is in contact with the surface of the electronic multi-touch floor covering. An entity record is then retrieved from a data store, such as a database, with the retrieved entity record corresponding to the identified shape. Actions are then retrieved from a second data store with the actions corresponding to the retrieved entity record. The retrieved actions are then executed by the computer system. For instance, if the system detects that the family dog has entered an area that is "off-limits" for it, a notification to the owner can be dispatched in order to have the dog removed from the off-limits location.

U.S. Pat. No. 6,515,586 relates to a floor covering integrated with a tactile sensory layer so as to form a tactile sensory surface. The tactile sensory layer has a plurality of sensors arranged in a dense two-dimensional array. A controller is connected to the tactile sensory surface to track a person or object. The tactile sensory surface may be flexible and manufactured in bulk on a roll, so that it is adjustable in both length and width.

US 2006/0171570 discloses a "smartmat" that monitors and identifies people, animals and other objects. Objects are differentiated based on weight, footprint and floor/wall pressure patterns such as footfall patterns of pedestrians and other patterns.

Technical Problem

It is an object of an aspect of the present invention to provide a novel monitoring system, in particular, but not exclusively, a room occupant monitoring system.

GENERAL DESCRIPTION

According to preferred aspects of the invention, a monitoring system comprises:

a preferably resilient floor covering (flooring) having installed therein or thereunder a sheet-type pressure sensor;

and a sensor control unit connected to the sheet-type pressure sensor, including:

an analog-to-digital converter for converting an analog signal provided by the pressure sensor into a digital raw signal, a microcontroller connected to the analog-to-digital converter for receiving the digital raw signal, the microcontroller being configured to carry out data extraction by signal processing of the digital raw signal and generating a digital processed signal having a lower digital bandwidth than the digital raw signal, the digital processed signal carrying data extracted during the processing of the digital raw signal;

and a communications module connected to or integrated within the microcontroller so as to receive the digital processed signal, the communications module being configured to establish data communication with one or more database servers and to transmit the extracted data to the one or more database servers.

Preferably, the floor covering or flooring comprises or consists of a resilient multilayer or monolayer flooring laid out continuously (sheet flooring) or consisting of individual flooring elements (flooring tiles or planks). Preferably, the resilient multilayer or monolayer flooring is installed in lasting ("permanent") manner (the targeted lifetime being several years). The monolayer or multilayer flooring preferably has a decorative top surface.

A multilayer flooring used in the context of the invention preferably comprises one or more core or backing layers (hidden by a print layer when the flooring has been installed), a print layer (a thin printing substrate, the layer(s) of ink) and one or more transparent layers (top coating and/or wear layer) on top of the print layer. Printing may be effected on a dedicated substrate (e.g. a web of paper or polymeric material), which is laminated, or otherwise combined, with the other layers. Alternatively, one could directly print on one of the structural layers (e.g. a core or backing layer) or on the back of the wear layer.

The sheet-type pressure sensor preferably comprises a ferroelectret polymer film sandwiched between a first electrode layer and a second electrode layer. As used herein, the term "ferroelectret polymer film" designates a cellular polymer film structure that exhibits piezoelectric properties and, more specifically, that generates an electric potential difference between first and second electrode layers applied on its surfaces in response to pressure being applied on the polymer film structure. The "analog signal provided by the pressure sensor" designates the analog signal that is applied to the input of the analog-to-digital converter (ADC), possibly after signal conditioning (e.g. filtering or smoothing) by electric or electronic components. The "digital raw signal" is the digital signal delivered by the ADC, prior to any signal shaping, processing or data extraction in the digital domain. The "digital processed signal" carries the data extracted from the digital raw signal. The "communications module" designates a hardware module (e.g. a card, an adapter or controller) that implements the electronic circuitry required to communicate using a specific physical layer and data link layer standard such as Ethernet, Wi-Fi, Bluetooth, etc.

The ADC is preferably configured to sample the analog signal at a sampling rate comprised in the range from 50 Hz to 1 kHz, more preferably in the range from 50 Hz to 500 Hz and yet more preferably in the range from 100 Hz to 200 Hz.

The resolution of the ADC is preferably at least 8 bits ($2^8=256$ quantization levels), more preferably at least 12 bits ($2^{12}$ quantization levels) and yet more preferably at least 16 bits ($2^{16}$ quantization levels). Advantageously, the ADC is connected to the pressure sensor via a charge amplifier and a low-pass filter. The low-pass filter preferably has a cutoff frequency of 200 Hz or below, more preferably 100 Hz or below.

According to a preferred embodiment of the invention, the microcontroller is configured to detect fall events (of a person, e.g. the room occupant) through the processing of the digital raw signal. The routine for detection of a fall event may comprise feature extraction from the digital raw signal. The microcontroller may be configured to rate the different monitored quantities according to a predefined rating scheme, the ratings reflecting the probability or the plausibility of occurrence of the value of each monitored quantity in the event of a fall. The microcontroller may further be configured to conclude to a positive detection of a fall event in a time window if the cumulated rating, reflecting the probability that a fall has occurred, exceeds a certain threshold.

According to a preferred aspect of the present invention, the monitoring system comprises a building automation system actuator for controlling operation of an electric appliance of a building automation system (BAS). Another term frequently used for BAS is BMS (building management system). In this context, the term "BAS actuator" designates an adapter that interfaces the monitoring system with the BAS and allows the monitoring device to control at least one appliance, e.g. lighting, air conditioning, roller shutters, ventilation, air conditioning or the like. For instance, the monitoring system could be configured to switch on room lighting at nighttime if it detects that a person is walking in the room. Additionally or alternatively, the monitoring system could be configured, in case it detects a fall, to give the fallen person a feedback that the fall has been detected and that the caregivers have been informed. Such feedback could e.g. be given via the room lighting (by making it blink), via a dedicated visual indicator, or via loudspeaker.

In addition to an interface with a BAS, or as an alternative thereto, the monitoring system may comprise a relay for controlling operation of an electric load (e.g. a light, an electric bell, a roller shutter motor, ventilation, air conditioning, etc.) For instance, a relay of the monitoring system could be connected in parallel to a nurse call button or a light switch. The monitoring system could thus initiate a nurse call or switch on a light depending on the data extracted by the microcontroller. If, for instance, the monitoring system detects a fall, it may trigger the nurse call via the corresponding relay. At the same time, or subsequently, it may provide a visual feedback to the fallen person by causing a light in the room to blink. Providing the monitoring system with one or more relays is advantageous since not all buildings and caretaking facilities are yet equipped with BASs. Furthermore, there may be buildings where a BAS and a conventional electric power network coexist.

According to a preferred embodiment of the invention, the monitoring system comprises a skirting, having illumination devices (incandescent lamps, LEDs or OLEDs) integrated therein that are connected with and controllable by the building automation system actuator or the relay.

Instead of a single pressure sensor, the floor covering may have installed therein or thereunder plural sheet-type pressure sensors, each comprising a ferroelectret polymer film sandwiched between a first electrode layer and a second electrode layer and connected to the sensor control unit, the sheet-type pressure sensors being arranged in substantially non-overlapping manner in different areas of a room partitioned into at least two partitions comprising at least a bedroom partition and a bathroom partition. In this preferred embodiment of the invention, the sensor control unit receives the analog signals from the different pressure sensors and converts them into corresponding digital raw signals. The microcontroller carries out the data extraction from the individual digital raw signals. The microcontroller may be configured to encode the extracted data on one or on plural digital processed signals.

The signal processing of the digital raw signal preferably comprises detection of events in the digital raw signal in accordance with predefined detection criteria. The detected events preferably include at least one, preferably at least two, of: falls, (walking) activity starts, (walking) activity ends, entries into the monitored room and exits out of the monitored room.

According to a preferred embodiment of the invention, the signal processing of the digital raw signal comprises detection of a heart beat signal and/or a respiration signal in the digital raw signal and determining a heartbeat rate and/or a respiration rate. Heart beat and/or a respiration signal detection may include, amongst others, low-pass filtering the raw digital signal and/or signal rectification of the signals.

Preferably, generating the digital processed signal comprises assembling datagrams or data packets containing each at least an identifier identifying the microcontroller, a time stamp and one or more of the extracted data, e.g. the detected events described by predefined event description codes.

The monitoring system preferably comprises the one or more database servers. The one or more database servers are advantageously configured to enter the extracted data in a database, to compute analytical data from the extracted data and to interface, preferably via a secure Internet connection, with client applications (client "apps" or client "dashboards") configured for visualizing the analytical data.

The one or more database servers may, furthermore, be configured to convert the extracted data into one or more discrete-time data (reflecting the state of the monitored room) at given times (e.g. every second, every 5 s, every 10 s, every 20 s, every 30 s, every minute, every 2 minutes, every 5 minutes, every 10 minutes, every 15 minutes, every 30 minutes or every hour) so as to generate a timeline, to log the discrete-time data signals in the database and to make the discrete-time data available to the client applications as part of the analytical data.

The one or more database servers are preferably configured to also compute statistical indicators relating to the extracted data and/or to the discrete-time date, to log the statistical indicators in the database and to make the statistical indicators available to the client applications as part of the analytical data.

The one or more database servers may be configured to stream at least part of the analytical data to the client applications. Additionally or alternatively, the one or more database servers may be configured to transmit at least part of the analytical data to the client applications upon receiving requests issued by them or upon being polled by them.

The one or more database servers may be configured to detect at least one of a potential emergency situation, such as, e.g. an unauthorized leave of a person from the monitored room, an unauthorized intrusion into the monitored room, a fall, a sudden health degradation of the person in the monitored room, etc., based on a short-time analysis of the extracted data or a potential creeping health degradation of the person in the monitored room based on a long-time analysis of the extracted data. In the context of the present document, "short-time analysis" means an analysis of data in a time window of not more than 5 minutes, preferably not more than 2 minutes, more preferably not more than 1 minute, and possibly not more than 30 s, 20 s, 15 s, 10 s, 5 s, 2 s, 1.5 s or even less. "Long-time analysis" means, in the context of the present document, an analysis of data collected over a time of not less than 1 hour, preferably not less than 2 hours; long-time analysis of data may also stretch over several days, weeks, months or even years of data if such long-time observations are available.

A particularly preferred embodiment of the invention relates to a monitoring system implemented as a room occupant monitoring system in a caretaking institution, such as, e.g., a hospital, a nursing home or a retirement home, or a penal institution. The room occupant monitoring system comprises a floor covering (flooring) having installed therein or thereunder plural sheet-type pressure sensors of the above-specified type, the sheet-type pressure sensors being arranged in different areas of a room substantially without overlap, the room being partitioned into at least two partitions comprising at least a bedroom partition and a bathroom partition. According to the particularly preferred embodiment, the signal processing of the digital raw signal comprises detection of activation events, including at least two of suspected falls, activity starts, activity ends, suspected entries and suspected exits, in the digital raw signal in accordance with detection criteria. Furthermore, generating the digital processed signal comprises assembling datagrams or data packets containing each at least an identifier identifying the microcontroller, a time stamp and one or more of the data extracted from raw signals from the different pressure sensors. Still according to the particularly preferred embodiment, one or more database servers are provided, which are configured to enter the extracted data in a database, to compute analytical data from the extracted data, to interface with client applications configured for visualizing the analytical data, to convert the extracted data into one or more discrete-time data, to log those discrete-time data in the database, to make the discrete-time data available to the client applications as part of the analytical data, to compute statistical indicators relating to the extracted data, to log the statistical indicators in the database and to make the statistical indicators available to the client applications as part of the analytical data. The one or more database servers of the room occupant monitoring system are preferably configured to stream at least part of the analytical data to the client applications and/or are preferably configured to detect at least one of an unauthorized leave, an unauthorized intrusion, a fall, a sudden health degradation, etc., based on short-time analysis of the extracted data or a potential creeping health degradation based on long-time analysis of the extracted data.

A noteworthy advantage of the present invention resides in the fact that the monitored person or the person in the monitored room is not required to wear a wearable device (for measuring pulse, respiratory rate and/or other parameters). This greatly reduces the perceived impact on the monitored person's life. According to preferred embodiments of the invention, the monitoring system thus does not comprise any such wearable device. It should be noted however, that it is not excluded to use the present monitoring system in combination with one or more other monitoring systems in case a closer and/or more advanced (medical) monitoring of the person is intended or necessary. More specifically, the present monitoring system does not aim at replacing medical vital signs monitoring systems but at offering a monitoring solution especially (but not exclusively) for situations where permanent medical monitoring of vital signs is not necessary but monitoring the person's activity is desirable. It will be appreciated that the system according to the invention bridges that gap in a relatively non-intrusive manner with regard to the monitored person's private life.

According to preferred embodiments of the invention, the film-type pressure sensor and, optionally, its connectors are sealed within a water-tight envelope. It will further be appreciated that the system proposed is insensitive to moisture and humidity (unlike systems based on capacitive sensing). Accordingly, the floor covering including the sensor can be used in bathrooms, kitchens or rooms which must be regularly cleaned with a detergent.

Embodiments of the monitoring system offer long and short term health monitoring functionality. The monitoring system may comprise alerting features. Wellness of a monitored individual may be assessed on the basis of the individual's levels of activity during day and night. High activity during the day and low activity during the night is typically indicative of good health. Accordingly, when the ratio of day to night activity follows a decreasing trend, the system may issue a corresponding warning to the caregivers, who may then try to identify the reasons for the trend as well as to take measures that aim at restoring the patient's health condition.

In contrast to systems that rely on worn devices, and which thus require a minimum amount of the monitored person's ability and willingness to collaborate, the monitoring system according to the invention requires no specific education of the persons to be monitored. It happens quite often that patients refuse to wear a monitoring device. The reasons for refusal may be discomfort or fear from being stigmatised as a person having to be monitored. Experience shows that it may be even more difficult to encourage a person to carry a wearable device when the person feels healthy. In that respect, the present invention thus greatly simplifies the caregivers' task.

The system according to the invention may be configured to address multiple problems simultaneously. First, the monitoring system permits the detection of emergency conditions, especially if the monitored person has fallen. Second, activity monitoring by the monitoring system allows an assessment of the monitored persons' heath conditions. The database may be configured to learn the person-specific activity patterns and to trigger an alert or message informing the caregivers about any significant deviation from the expected activity pattern or a particular trend in the activity pattern. That feature may promote the early detection of diseases.

BRIEF DESCRIPTION OF THE DRAWINGS

By way of example, a preferred, non-limiting embodiment of the invention will be described in detail with reference to the accompanying drawings, in which.

DETAILED DESCRIPTION OF ONE OR MORE PREFERRED EMBODIMENTS

Figure 1:
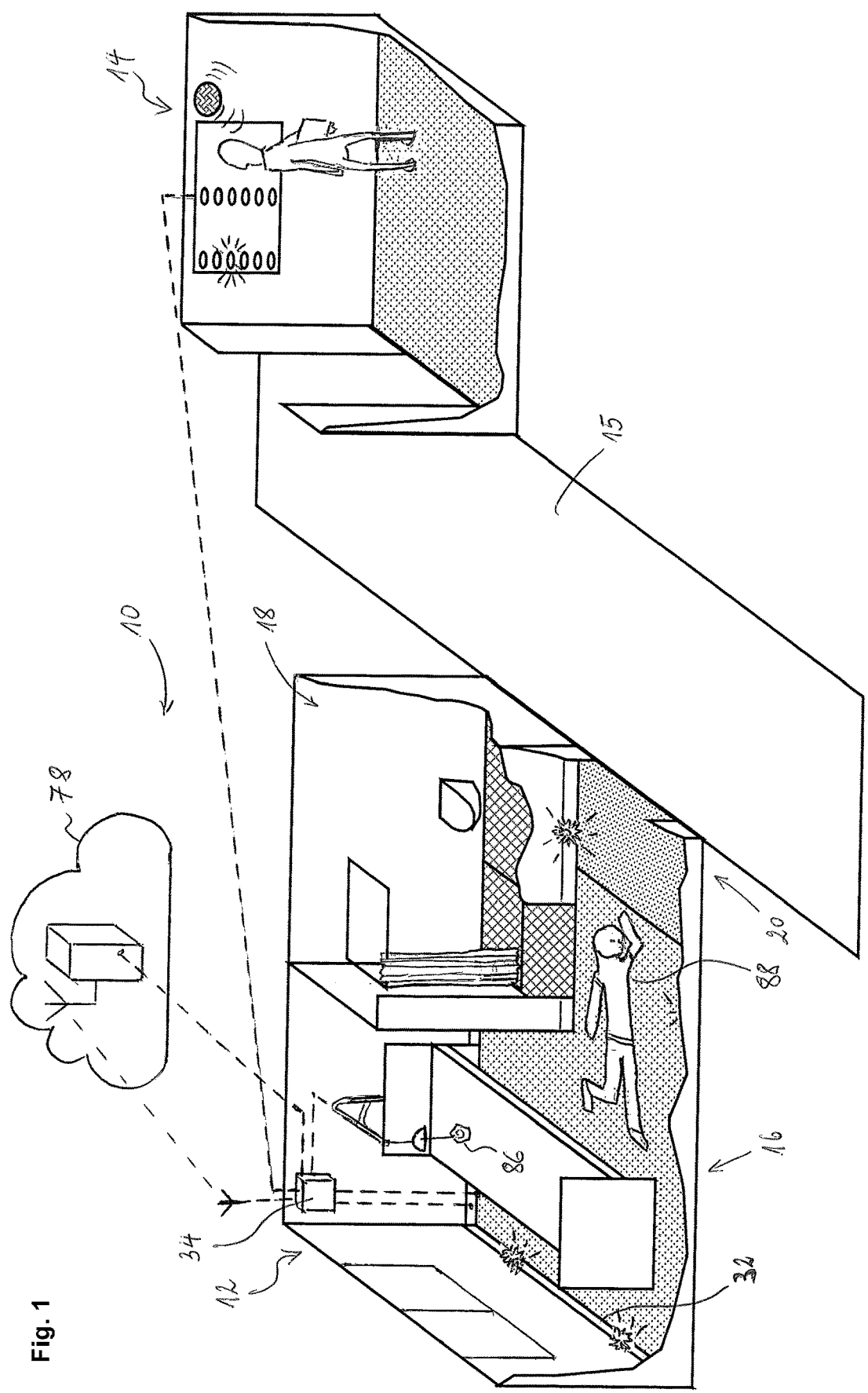
FIG. 1: is a schematic view of a room occupant monitoring system in a caretaking facility.

FIG. 1 schematically illustrates a room occupant monitoring system 10 in a caretaking facility, such as, in the present case, a retirement home or a hospital. There are shown a room 12 of a person to be monitored, a caregivers' room 14 and a hallway or corridor 15 linking those rooms. The retirement home or hospital may, of course, comprise further rooms, but these are not shown for sake of clarity of the drawing. The room 12 comprises a main, bedroom, partition 16 and a, bathroom, partition 18. The room 12 is accessible from the hallway or corridor 15 via an entrance/exit zone 20, which is adjacent the door (not shown) of the room 12.

Figure 2:
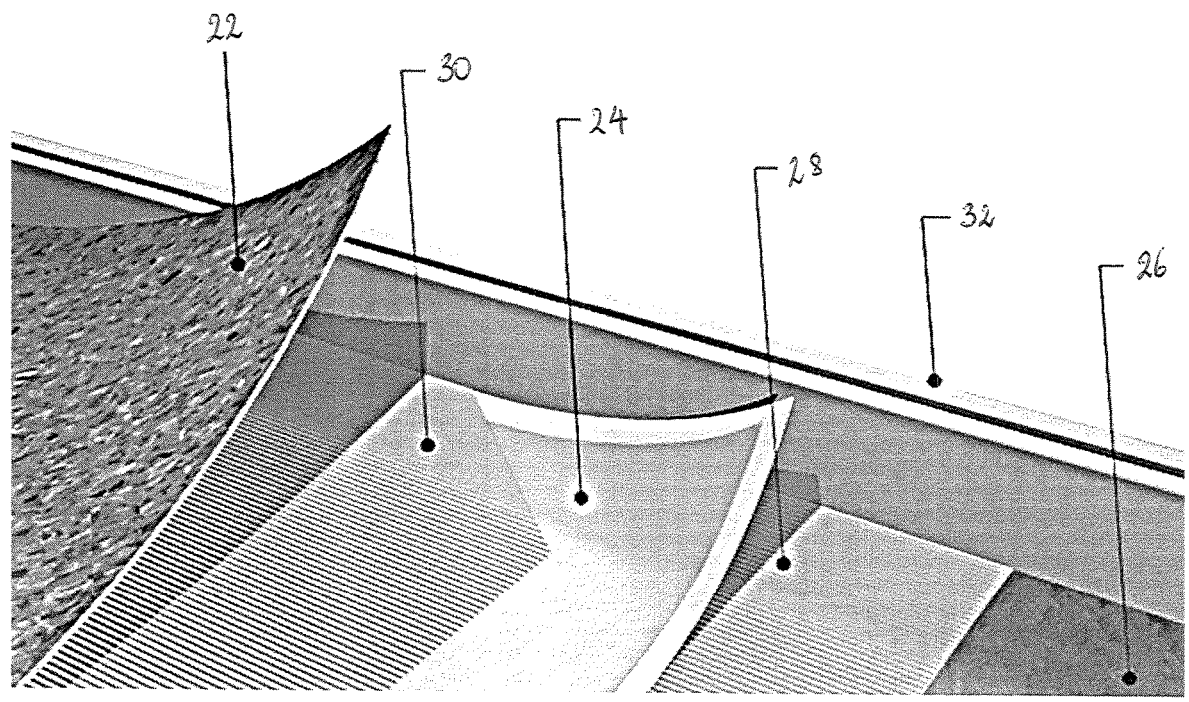
FIG. 2: is a perspective illustration of the construction of a floor covering comprising a sheet-type pressure sensor.

The room occupant monitoring system 10 comprises a resilient polymer-based floor covering 22 having installed thereunder plural sheet-type pressure sensors 24. The construction of the floor covering is best illustrated in FIG. 2. The sheet-type pressure sensor 24 is affixed to the floor pavement 26 with a first adhesive layer 28. The resilient floor covering is affixed on the top surface of the sheet-type pressure sensor 24 with a second adhesive layer 30. Also shown in FIG. 2 is a skirting 32 that features LED illumination.

The sheet-type pressure sensors 24, which may be configured as flexible tiles, planks, stripes or bands, are arranged substantially without overlap with one another. In each zone of the room, the sheet-type pressure sensors 24 are connected in parallel to the sensor control unit 34, in such a way that the analog signals originating from different sensors within the same zone are not readily discernable by the sensor control unit 34. The sensors of a given zone are hereinafter referred to collectively as "sensor group". The different sensor groups, each associated to a different zone of the room, are, however, connected individually to the sensor control unit 34, whereby it is known which sensor group an analog signal originates from. In the embodiment illustrated in FIG. 1, there is one sensor group for each one of the following zones: 1) entrance/exit zone 20, 2) bedroom partition 16 and 3) bathroom partition 18.

Figure 3:
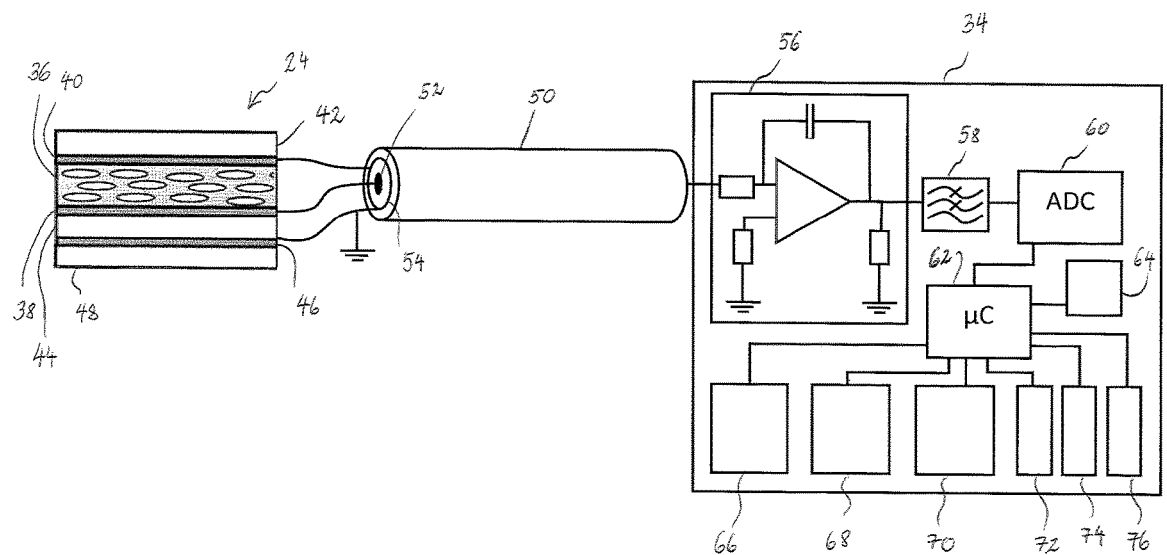
FIG. 3: is a schematic of a ferroelectret-based pressure sensor and a sensor control unit connected thereto.

FIG. 3 schematically illustrates the sensor control unit 34 and how it is connected to one sheet-type pressure sensor 24. The sheet-type pressure sensor 24 comprises a ferroelectret polymer film 36 sandwiched between a first electrode 38 and a second electrode 40. When the ferroelectret polymer film 36 is compressed, a voltage is generated between the first and the second electrodes 38, 40. That voltage is input to the sensor control unit 34, which converts it into a digital signal for further treatment. A first electrically insulating film 42 is arranged on the second electrode 40 and a second electrically insulating film 44 is arranged between the first electrode 38 and a shield electrode 46. A third electrically insulating film 48 is applied on the opposite side of the shield electrode 46. The second electrode 40 and the shield electrode 46 are connected to ground, in such a way as to shield the first electrode 38, which is the signal electrode of the sensor, from external electromagnetic interference. In the illustrated embodiment, the electrodes 38, 40 and 46 are aluminum layers with a thickness of 5 to 20 µm (e.g. 9 µm) each. The ferroelectret polymer film 36 has a thickness preferably comprised in the range from 50 to 100 µm (e.g. 65 µm). The electrically insulating films 42, 44, 48 can be made of PET (polyethylene terephthalate) or any other electrically insulating polymer. Their thicknesses preferably amount to 50 to 250 µm (e.g. 75 µm). The total thickness of the sheet-type pressure sensor 24 thus amounts to less than 1 mm. The signal electrode (first electrode 38) may be patterned by insulating regions, which preferably extend along straight axes. Those regions allow the pressure sensor to be cut to a desired shape with a reduced risk that the cutting will cause short-circuits between the signal electrode 38 and one of the grounded electrodes 40, 46.

The pressure sensor 24 is connected to the sensor control unit 34 by a coaxial cable 50 comprising a core conductor 52 and at least one shield conductor 54 surrounding the core conductor 52. The core conductor 52 is connected to the signal electrode 38, whereas the shield conductor 54 is connected to the grounded electrodes 40, 46. The other end of the core conductor is connected to a charge amplifier 56. The analog signal output by the charge amplifier 56 is filtered by a low-pass filter 58 and input to an ADC 60, which preferably operates at a sampling rate of 100 Hz to 200 Hz and with a resolution of at least 8 bits. The digital raw signal output by the ADC 60 is processed by the microcontroller 62. The microcontroller 62 comprises or is connected to a memory module 64, in which the firmware of the sensor control unit 34 is stored. The microcontroller 62 further comprises or is connected to communication modules, including, in the illustrated embodiment, an Ethernet communication module 66, a WiFi communication module 68 and a DECT (Digital Enhanced Cordless Telecommunications) communications module 70. Instead or in addition to a DECT communications module, the microcontroller 62 could, e.g., comprise or be connected to a GMS (Global System for Mobile Communication), GPRS (General Packet Radio Service), EDGE (Enhanced Data Rates for GSM Evolution), UMTS (Universal Mobile Telecommunications System) or the like, communications module. The microcontroller 62 also controls relays 72, 74, allowing it to switch on and off electric devices connected to the relays 72, 74. Finally, the sensor control unit 34 comprises a building automation system actuator 76, via which the microcontroller 62 may be interfaced with a BAS.

Figure 4:
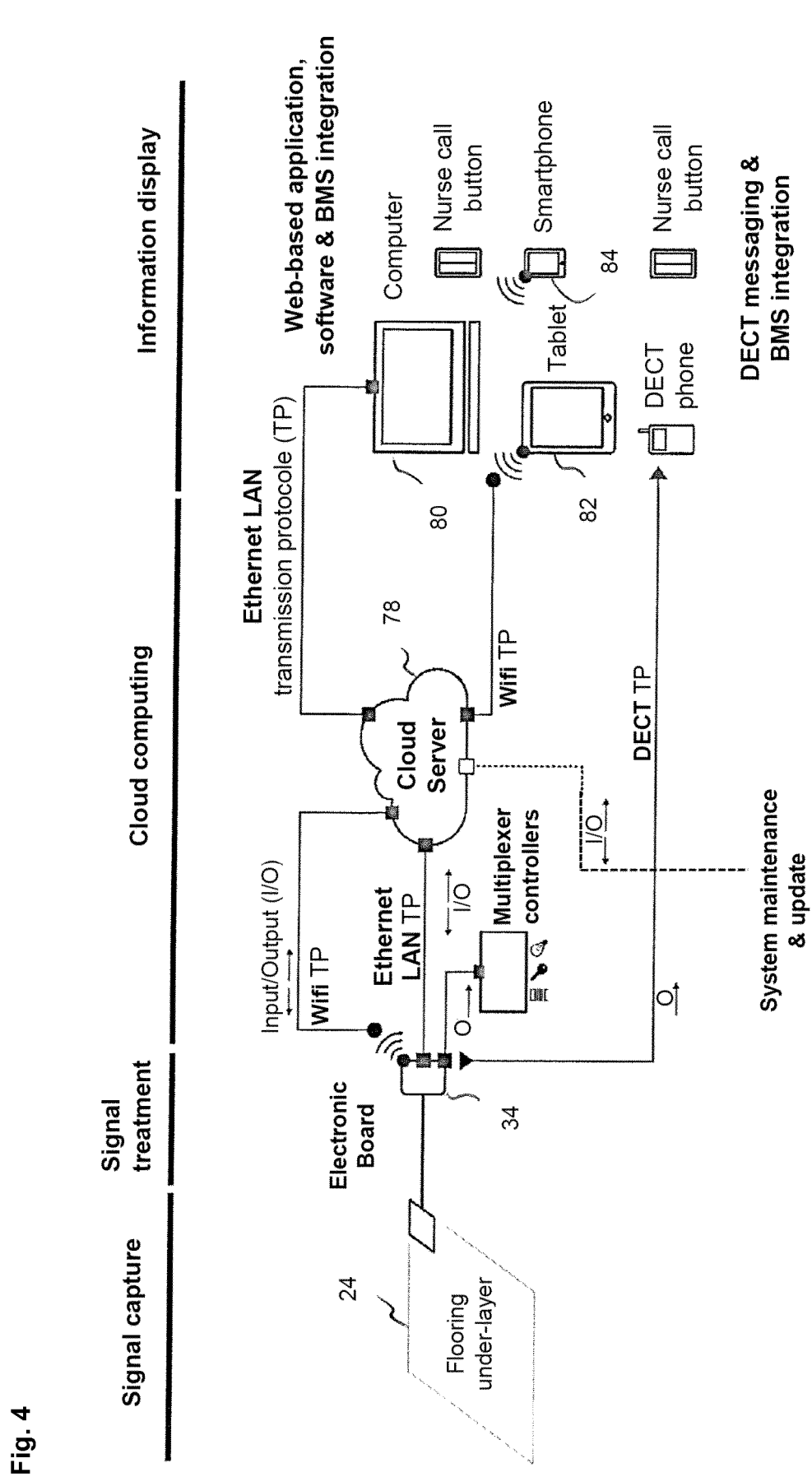
FIG. 4: is a high-level schematic layout of the monitoring system.

As best shown in FIGS. 1 and 4, the sensor control unit 34 (labelled "electronic board" in FIG. 4) is connected to a cloud server 78 via Ethernet and/or WiFi links. The cloud server 78 implements a database server administering a database, wherein the data received from the sensor control unit 34 are stored. As will be understood, in a typical application the cloud server 78 will be connected to several sensor control units 34 (from the same or different facilities.) Accordingly, the database will contain data from different rooms and relating to different room occupants. Nevertheless, since the data from different sensor control units 34 are typically processed independently from one another, for the purposes of the present, it will be sufficient to illustrate the analyses carried out with reference to a single sensor control unit 34.

Figure 5:
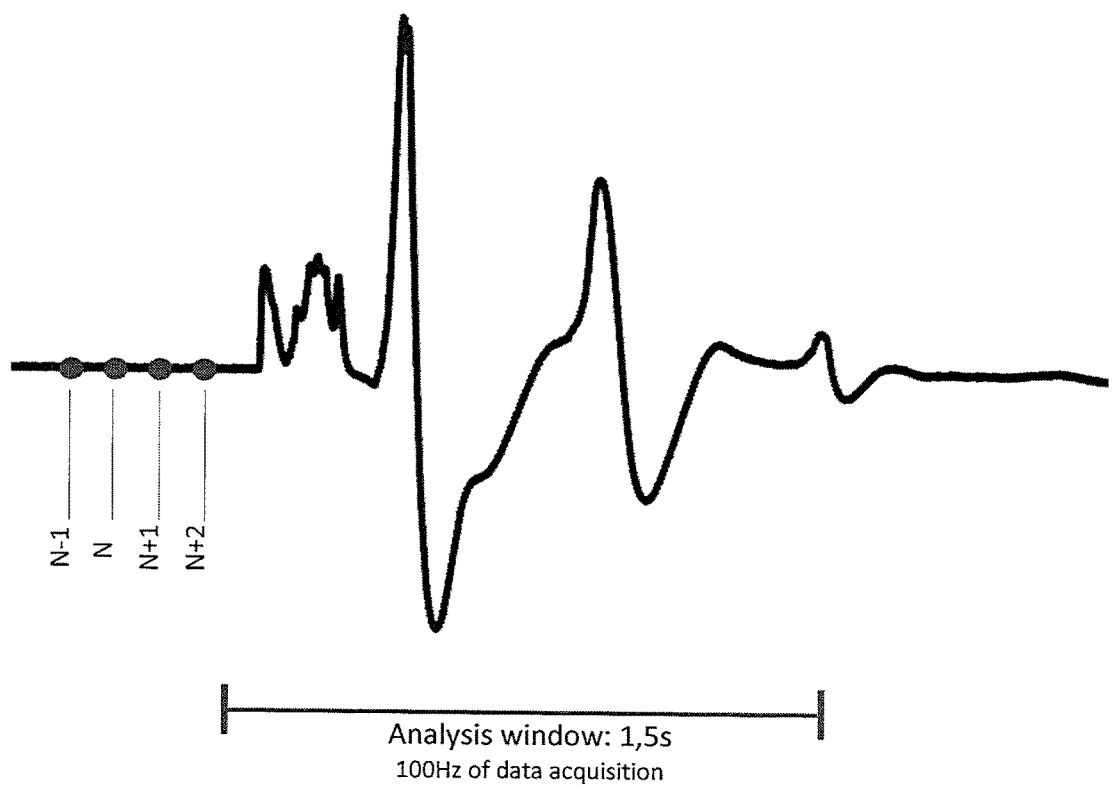
FIG. 5: is a screenshot of the digital raw signal after filtering but prior to data extraction.

The microcontroller 62 executes data extraction from the digital raw signal that it receives from the ADC 60. Data extraction includes searching the digital raw signal for patterns that correspond to predefined events that are to be detected. One event that has to be detected is a fall of a person in the room 12 being monitored. To this end, the microcontroller 62 continuously checks whether the signal within a time window of a predefined duration satisfies certain criteria predefined in the firmware. An example of an algorithm for fall detection is described with reference to FIG. 5, which shows a short portion of a digital raw signal measured at a time when a fall occurred in a monitored room.

The microcontroller continuously monitors certain parameters within a time window of a given duration. The monitored parameters are updated as the oldest sample leave the time window and a new sample enters it. The microcontroller checks whether each of the monitored parameters lies above or below a predefined threshold or within a predefined range. It concludes to a fall if predefined minimum requirements for a fall detection are met. For instance, the microcontroller may be configured to detect a fall if all of the monitored parameters lie within respective intervals. Alternatively, the microcontroller could calculate values indicating to what extent each parameter meets the corresponding criterion, compute the sum of these values and compare that sum with a threshold: if the threshold is exceeded, a fall is detected; if the threshold is not exceeded, no fall is detected. Of course, other heuristics for detection of a fall could be implemented as well.

Other events detected by the microcontroller may be the start of activity (walking) and the end of the same. Walking activity detection may e.g. be effected by the microcontroller comparing the energy parameter with a threshold. The microcontroller may e.g. be configured to detect the beginning of activity. Conversely, the microcontroller may detect the end of activity if it failed to detect any activity during the same period. Each time the microcontroller 62 detects one of these events, it assembles a datagram or data packet containing at least the ID of the sensor control unit, an identifier identifying the detected event, an identifier identifying the zone in which the event occurred and a time stamp indicating at what time the event was detected. Optionally, further indications may be included into the datagram or data packet, such as e.g. the parameters that led to the detection of the identified event. If several events occurred shortly one after the other, they may either be included into separate datagrams or data packets or grouped into one datagram or data packet.

The datagrams or data packets are transmitted to the cloud server 78 via the Ethernet link and/or the WiFi link. If a datagram or data packet is received by the cloud server 78, it acknowledges receipt of the sensor control unit 34 from which the datagram or data packet originated. In the absence of any acknowledgement of receipt, the microcontroller resends the datagram or data packet.

When detecting events, the microcontroller may take into account the digital raw signals from the different sensor groups. For instance, a fall occurring on the boundary of two sensor groups (e.g. in the passage from the bedroom to the bathroom) might not be detected as such if the signals of these sensor groups are only processed individually. The microcontroller may thus optionally check whether the sum of the digital raw signals from adjacent sensor groups contains a pattern corresponding to that of a fall. This kind of check may either be carried out continuously or only occasionally, e.g. each time a predefined condition on one or more of the monitored parameters is satisfied with regard to one or more of the sensor groups.

The microcontroller 62 keeps a local copy of any detected event in a cyclic buffer memory. The size of the buffer memory may be such that several days of data may be stored therein, in case of an interruption of the communication links between the sensor control unit and the cloud server.

The microcontroller 62 also comprises a clock, which it uses, inter alia, to time-stamp the datagrams or data packets.

In the illustrated embodiment, a synchronization of the local clock with "system time", which is kept by the cloud server or a clock server to which the cloud server is connected, is effected each time data are exchanged between the sensor control unit and the cloud server.

The sensor control unit 34 is configured to detect further the heart rate and/or the respiration rate of a person within the room. The microcontroller 62 may achieve this e.g. by performing Fast Fourier Transforms on sequences of squared digital raw signal samples representing several seconds of measurement (e.g. at least 20 or 30 s) and detecting spectral peaks within the spectral ranges of interest The detected heart rate and/or respiratory rate are preferably transmitted to the cloud server at regular intervals. That may be effected with a second type of datagrams or data packets or within the same datagrams or data packets that contain information about detected events.

As illustrated in FIG. 1, the sensor control unit is connected with the nurse or caregiver call system of the caretaking facility. Each room 12 is equipped with a nurse call button 86, which is typically arranged in such a way that the room occupant can reach it from their bed. In its basic configuration, actuation of the nurse call button closes an electrical circuit, which activates an audible and visual alarm signal in the caregivers' room 14. In this case, one of the relays 72, 74 of the sensor control unit 34 is connected in parallel to the nurse call button 86 in such a way that the microcontroller 62 can control the electrical circuit that gives the alarm. If the retirement home or hospital comprises a more modern nurse or caregiver call system, the sensor control system may be interfaced therewith via the BAS actuator 76, the DECT communications module 70, the Ethernet communication module 66 and/or the WiFi communication module 68. When the microcontroller 62 detects a fall of the room occupant 88 (as illustrated in FIG. 1), it triggers an alarm via the caretaking facility's nurse or caregiver call system. If the nurse or caregiver call system can deal with it, an emergency code, possibly indicating that the occupant has fallen, is sent as well, in order to communicate the urgency of the need for assistance. The sensor control unit 34 is further interfaced with the LEDs integrated in the skirting 32 of the room 12. When a fall is detected, the microcontroller 62 controls the LEDs in such a way that they generate a visual signal (e.g. blinking or flashing) that informs the room occupant that the fall has been detected and the alarm has been given. If the retirement home or hospital's nurse or caregiver call system features bi-directional communication, the microcontroller 62 may also inform the room occupant that the caregivers have acknowledged receipt of the alarm by emitting a second visual signal.

Giving feedback to the room occupant that their fall has been detected and that help is under way has the potential to greatly reduce psychological stress in case of a fall. It may furthermore somewhat reduce the room occupant's fear from getting up at nighttime. It is worthwhile noting that a knocking code (a predefined sequence of knocks and shorter or longer pauses) may be communicated to the room occupant in case they fall and the fall is not detected by the monitoring system. In this case, the microcontroller is configured to identify the knocking code in the analog signals and to trigger an alert in case of a positive detection. If the fallen person receives no visual feedback from the skirting that the fall has been detected, they may manually trigger the alarm by knocking the predefined knocking code into the floor.

The microcontroller may optionally be configured to trigger an alarm only if the fall is not followed, with a short period (e.g. in the range from 30 s to 2 minutes), by regular walking activity indicating that the person is able to move. In this case, the fall may be registered without leading to (immediate) intervention by the retirement home or hospital personnel.

The cloud server 78 receives the transmitted datagrams or data packets and stores the data contained therein (event information, heart rate, respiratory rate) in the database. The data are stored as received. The cloud server further converts the received data into discrete-time data reflecting the state of the monitored room at discrete times so as to generate a timeline. Specifically, when the cloud server receives the event "activity start (bedroom)", it logs the status "active in bedroom" each predefined time interval (e.g. each minute) until it receives the event "activity end (bedroom)" or "fall detected (bedroom)". Similarly, it logs the status "inactive" each predefined time interval until it receives one of the events "activity start (bedroom)", "activity start (bathroom) ", activity start (entrance/exit)" or any fall detection event. Each timeline is tied to a sensor control unit ID in the database, which permits to look up the status of each room at any past time. When heart rate and respiratory rate are measured by the sensor control unit, the cloud server also logs these data in the timeline.

Further to logging the data, the cloud server also allows client applications (e.g. a dashboard app) to visualize the data on a client device, such as e.g. a computer 80, a tablet computer 82, a smartphone 84, a phablet (not shown), etc. The data made available to the client applications may include analytical data such as the above-mentioned timelines and statistical indicators computed by the cloud server. The following statistical indicators may, e.g., be computed:

[a] Number of activity periods in the bathroom (per day, per night, etc.);
[b] Average of [a] over a longer period (e.g. one week, one month, etc.);
[c] Trend (derivative) of [a] or [b];
[d] Number of falls (per day, per night) in any or a specific zone of the room;
[e] Average of [d] over a longer period (e.g. one week, one month, etc.);
[f] Trend (derivative) of [d] or [e];
[g] Cumulated activity duration (per day, per night)
[h] Average of [g] over a longer period (e.g. one week, one month, etc.);
[i] Trend (derivative) of [g] or [h];
[j] Maximum heart rate each day;
[k] Average of [j] over a longer period (e.g. one week, one month, etc.);
[l] Trend (derivative) of [j] or [k];
[m] Minimum heart rate each day;
[n] Average of [m] over a longer period (e.g. one week, one month, etc.);
[o] Trend (derivative) of [m] or [n];
[p] Maximum breath rate each day;
[q] Average of [p] over a longer period (e.g. one week, one month, etc.);
[r] Trend (derivative) of [p] or [q];
[s] Minimum breath rate each day;
[t] Average of [s] over a longer period (e.g. one week, one month, etc.);
[u] Trend (derivative) of [s] or [t];
[v] Number of (unannounced or unauthorized) leaves per day or per night;

[w] Average of [v] over a longer period (e.g. one week, one month, etc.);
[x] Trend (derivative) of [v] or [w];
etc.

The cloud server may further analyze the distribution of the above indicators in time, carry out frequency analysis thereon, compute cross-correlations between different indicators, etc.

The client applications are preferably configured to visualize the analytical data in matrices, charts, histograms, or any other convenient manner.

The client application and/or the cloud server may be configured to carry out long-time analyses of the available data. Preferably, they are further configured to inform the user about emergency situations, abnormal events, potential heath degradations and any other situation that merits human intervention. The data processed by the cloud server and/or the client application could, e.g., be used to detect signs of an epileptic crisis, a heart attack, a diabetic crisis, etc.

For instance, the detection of a fall not followed by walking activity within a short period may cause the cloud server may push an alarm message to the applications having access to the data concerned informing the user that the person in the monitored room urgently requires help. An alarm message may also be automatically dispatched to a registered phone or pager number. That way, redundancy is added to the sensor control unit activating the nurse or caregiver call system of the hospital or retirement home.

Using the above-mentioned indicators, the cloud server and/or the client application may detect a creeping health degradation, which might otherwise remain undiscovered, at an earlier point in time. For instance, increasing (walking) activity could be indicative of insomnia; a rising number of stays in the bathroom could be a sign of e.g. a kidney disorder. It should be noted that the monitoring system according to the invention could assist medical personnel in the discovery of symptoms, whereas the diagnostic work itself remains within the responsibility of such personnel. One particular advantage of the monitoring system is that, regarding questions such as nighttime activity, daytime activity and toilet usage, medical personnel need not solely rely on the patients' responses, obtained by interrogations, which cannot always be trusted. The system as an additional source of objective information will be highly appreciated, for instance, in case of room occupants suffering from dementia (e.g. Alzheimer's disease), Parkinsonism or the like. It may further prove its usefulness in (early) diagnosis of those diseases, especially regarding the detection of symptoms.

Preferably, the cloud server and/or the client application includes one or more subsystem for determining abnormalities in the daily activity patterns of the monitored persons. The subsystem may be configured to learn the normal activity pattern (represented e.g. as a vector of observations in a multi-dimensional feature space) of each monitored person during an initialization phase and then assess how well the current activity patterns matches the learned pattern or a pattern predicted from the past observations. An indicator of how well two patterns match may be a suitably defined distance (metric) between those patterns in the feature space. The subsystem may be configured to detect an abnormality if the distance between the current activity pattern and the expected or stored activity pattern exceeds a predefined threshold. If the subsystem finds an abnormality, the cloud server and/or the client application issue a corresponding alert to the caregivers. Such an alert could be issued as text message using the short message service and/or as a popup window in the client application. The client application preferably gives the caretakers the possibility of acknowledging receipt of the alert and/or feedback on the monitored person's actual condition. That feedback may then be taken into account for the further monitoring. For instance, if the caregiver confirms the abnormality of the detected situation, the corresponding pattern(s) may be barred by the subsystem from being taken into account for calculation of the "normal" pattern. In that way it may be avoided that abnormal patterns progressively contaminate what the subsystem regards as normal. On the other hand, if the caregiver's feedback is that there was a false alert, the subsystem may take that information into account in order to become more tolerant and/or more robust against outliers. The subsystem is preferably also configured to monitor how the detected patterns evolve in feature space on the long term. It may be specifically configured to detect long-term drifts of the detected patterns and issue a corresponding warning to the caregivers via the client application. Preferably, the drift that caused the warning to be issued is graphically visualized to the caregiver, so that they will be able to more easily investigate the cause of the warning.

The monitoring system may further be used for other functions, such as, e.g. control of ambient lighting, of way-finding e.g. to the exit or to the bathroom. The monitoring system according to the illustrated embodiment is configured to switch on the LEDs of the skirting 32, when the microcontroller detects that the room occupant has put a foot on the floor. For the control of domotic actions (e.g. switching on and off of bathroom lighting, control of window shades, control of the bathroom heater, etc.) the sensor control unit 34 is preferably connected to a BAS of the retirement home or hospital.

Figure 6:
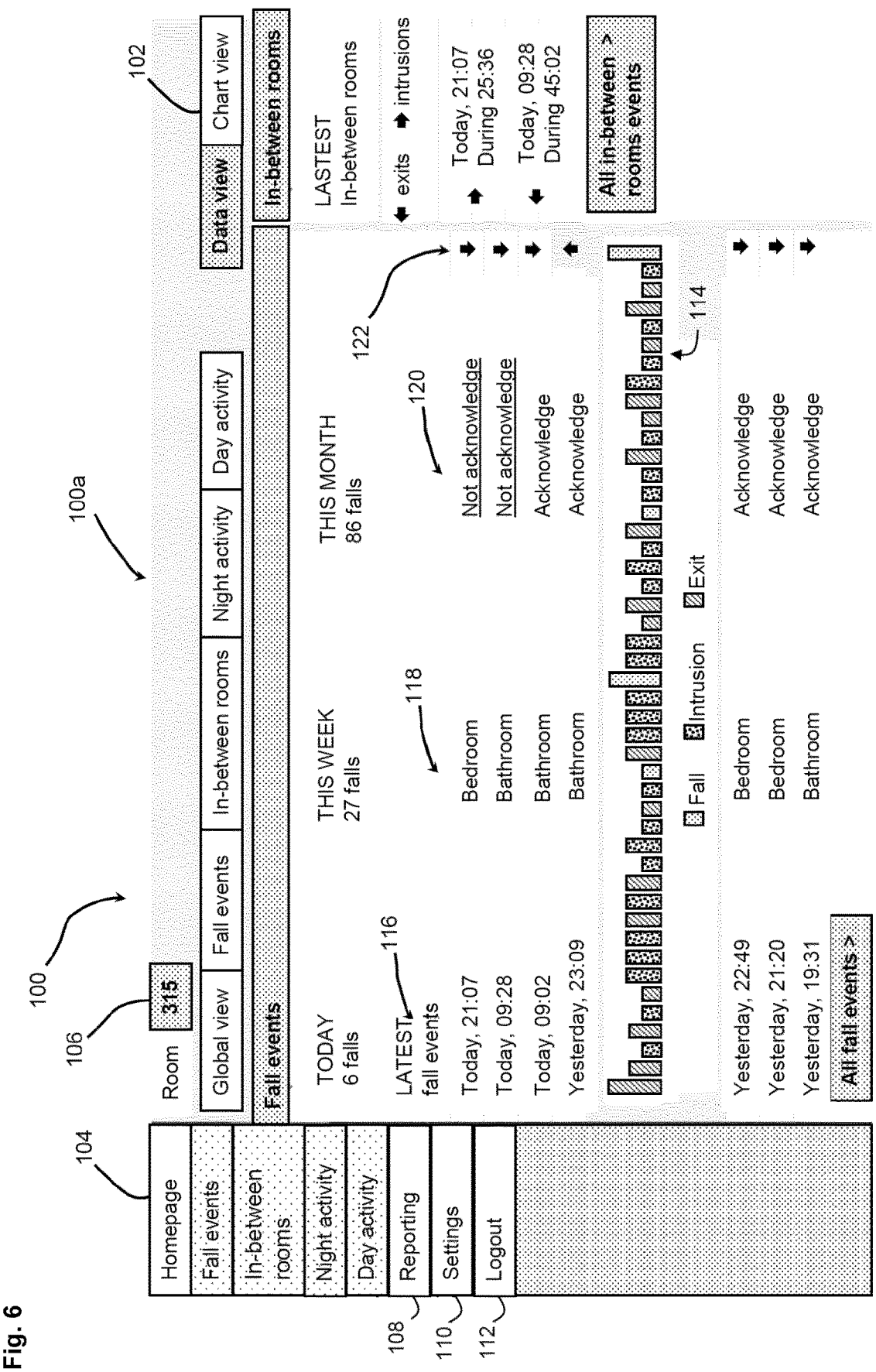
FIG. 6: is a screenshot of a first screen of an example of a client application for visualizing data collected by a room monitoring system according to the invention.
Figure 7:
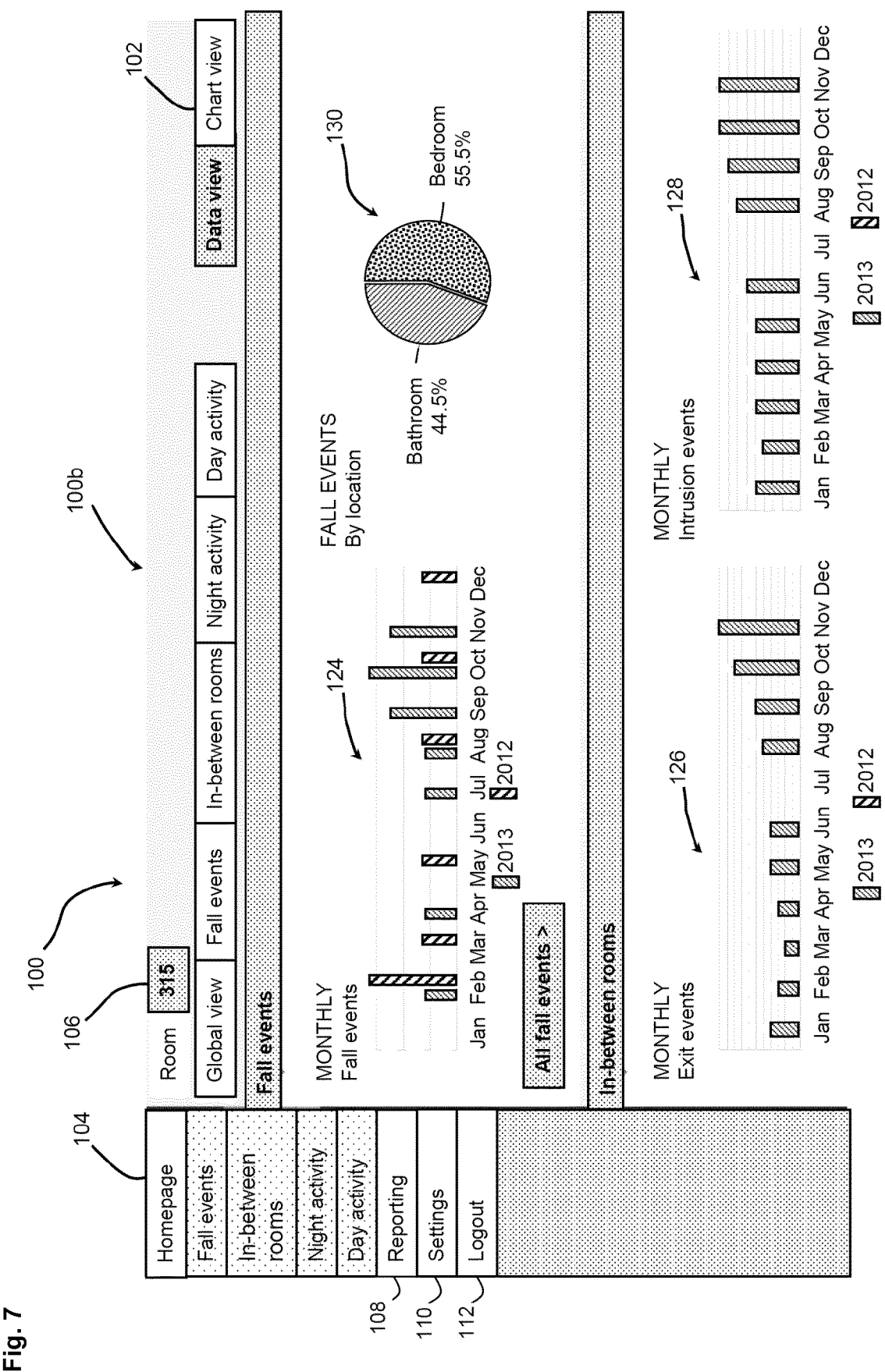
FIG. 7: is a screenshot of a second screen of the client application.

FIG. 6 and FIG. 7 are screenshots taken from a possible embodiment of a client application, which visualized the data made available by the cloud server to an end user. The client application is configured an interactive dashboard 100 or graphical user interface. The dashboard 100 comprises two main views, one being the so-called "data view" 100a (FIG. 6), the other being the so-called "chart view" 100b (FIG. 7). A control button 102 allows the user to easily toggle between the two views.

The dashboard comprises a navigation pane 104, which is available both in "data view" and in "chart view". The navigation pane 104 contains shortcuts to different categories of data, such as "fall events", "in-between rooms" (intrusions and exits), "night activity" and "day activity". A further link is provided to the "homepage", which allows the user to display information relating to the client application in general as well as to select the room number 106, of which the data are to be visualized. The navigation pane 104 also comprises a control 108 allowing to generate a preconfigured report, a control 110 giving access to a settings panel and a logout button 112.

In "data view" 100a, the dashboard gives an overview of individual events detected by the system in reverse chronological order (most recent events on top). Each event is characterized by its nature (e.g. "fall", "intrusion" or "exit"), its time stamp 116 and the location 118 where it occurred. Each event further comprises a status 120 ("acknowledged" or "not acknowledged") indicating whether the event has been taken into account by one of the users.

Each event can be visualized in the context of the event history by clicking on a drop-down control 122. Upon clicking the drop-down control, a drop-down section is opened, in which a timeline 114 displays all events recorded in a time window including the relevant event. The default length of the time window is adjustable in the settings panel. Furthermore, the dashboard may be configured to allow zooming in and out by hovering the cursor over the point in time of interest and turning the mouse wheel. When zooming in, the granularity of the timeline 114 becomes finer and finer until all events are resolved individually. When zooming out, adjacent time intervals are collapsed and the events contained therein are represented by a single bar, the height of which indicates the number of events it stands for.

It is worthwhile noting that the categories available in the navigation pane as well as their underlying data selection criteria may be configured by a system administrator and/or by the user (if the user has been given the corresponding authorization).

In "chart view" 100b, the dashboard gives an overview of statistical data. The default layout of the chart view can be configured by the user or at system administrator level, such that relevant information is made readily available. In the illustrated example, the "chart view" displays graphs 124, 126, 128 allowing a comparison between the frequencies of events of the same type recorded in two different years. Furthermore, a pie-chart 130 illustrates how the recorded fall events are distributed by location.

While a specific embodiment of the invention has been described herein in detail, those skilled in the art will appreciate that various modifications and alternatives to those details could be developed in light of the overall teachings of the disclosure. Accordingly, the particular arrangements disclosed are meant to be illustrative only and not limiting as to the scope of the invention, which is to be given the full breadth of the appended claims and any and all equivalents thereof.

The invention claimed is:

1. A monitoring system, comprising
   a floor covering having installed therein or thereunder a sheet-type pressure sensor;
   a sensor control unit connected to said sheet-type pressure sensor, including
   an analog-to-digital converter for converting analog signals provided by said pressure sensor into a digital raw signal,
   a microcontroller connected to said analog-to-digital converter for receiving said digital raw signal, said microcontroller being configured to carry out data extraction by signal processing of said digital raw signal and generating a digital processed signal having a lower digital bandwidth than said digital raw signal, said digital processed signal carrying data extracted during the processing of said digital raw signal;
   a communications module connected to or integrated within said microcontroller so as to receive said digital processed signal, said communications module being configured to establish data communication with one or more database servers and to transmit said extracted data to said one or more database servers;
   wherein said sheet-type pressure sensor comprises a ferroelectret polymer film, comprising a cellular polymer film structure exhibiting piezoelectric properties, the ferroelectret polymer film being sandwiched between a first electrode layer and a second electrode layer; and
   wherein a first electrically insulating film is arranged on the second electrode and a second electrically insulating film is arranged between the first electrode and a shield electrode.

2. The monitoring system as claimed in claim 1, further comprising a building automation system actuator for controlling operation of an electric appliance of a building automation system.

3. The monitoring system as claimed in claim 1, further comprising a relay for controlling operation of an electric load in an electric supply network.

4. The monitoring system as claimed in claim 2, comprising a wall skirting, said skirting having illumination devices integrated therein, said illumination devices being connected with and controllable by said building automation system actuator.

5. The monitoring system as claimed in claim 1, wherein said floor covering has installed therein or thereunder plural sheet-type pressure sensors, each comprising ferroelectret polymer film, comprising a cellular polymer film structure exhibiting piezoelectric properties, the ferroelectret polymer film sandwiched between a first electrode layer and a second electrode layer and connected to said sensor control unit, said sheet-type pressure sensors being arranged in a substantially non-overlapping manner in different areas of a room partitioned into at least two partitions comprising at least a bedroom partition and a bathroom partition.

6. The monitoring system as claimed in claim 1, wherein said signal processing of said digital raw signal comprises detection of activation events, including at least one, preferably at least two, of suspected falls, activity starts, activity ends, suspected entries and suspected exits, in said digital raw signal in accordance with detection criteria.

7. The monitoring system as claimed in claim 1, wherein said signal processing of said digital raw signal comprises detection of a heart beat signal and/or a respiration signal in said digital raw signal and determining a heartbeat rate and/or a respiration rate.

8. The monitoring system as claimed in claim 1, wherein generating said digital processed signal comprises assembling datagrams or data packets each containing at least an identifier identifying said microcontroller, a time stamp and one or more of said extracted data.

9. The monitoring system as claimed in claim 1, comprising said one or more database servers, said one or more database servers being configured to enter said extracted data in a database, to compute analytical data from said extracted data and to interface with client applications configured for visualizing said analytical data.

10. The monitoring system as claimed in claim 9, wherein said one or more database servers are configured to convert said extracted data into one or more discrete-time data, to log said discrete-time data in said database and to make said discrete-time data available to said client applications as part of said analytical data.

11. The monitoring system as claimed in claim 9, wherein said one or more database servers are configured to compute statistical indicators relating to said extracted data, to log said statistical indicators in said database and to make said statistical indicators available to said client applications as part of said analytical data.

12. The monitoring system as claimed in claim 9, wherein said one or more database servers are configured to stream at least part of said analytical data to said client applications.

13. The monitoring system as claimed in claim 9, wherein said one or more database servers are configured to detect at least one of a potential emergency situation, based on a short-time analysis of said extracted data, or a potential creeping health degradation based on a long time analysis of said extracted data.

14. The monitoring system as claimed in claim 1, implemented as a room occupant monitoring system in a hospital or a nursing home or a retirement home or a penal institution, the monitoring system comprising said one or more database servers,
- wherein said floor covering has installed therein or thereunder plural sheet-type pressure sensors, each comprising a ferroelectret polymer film comprising a cellular polymer film structure exhibiting piezoelectric properties sandwiched between, and in direct contact with, a first electrode layer and a second electrode layer and connected to said sensor control unit, said sheet-type pressure sensors being arranged in a substantially non-overlapping manner in different areas of a room partitioned into at least two partitions comprising at least a bedroom partition and a bathroom partition;
- wherein said signal processing of said digital raw signal comprises detection of activation events, including at least one, preferably at least two, of suspected falls, activity starts, activity ends, suspected entries and suspected exits, in said digital raw signal in accordance with detection criteria;
- wherein generating said digital processed signal comprises assembling datagrams or data packets, each datagram or data packet containing at least an identifier identifying said microcontroller, a time stamp and one or more of said extracted data;
- wherein said one or more database servers are configured to enter said extracted data in a database, to compute analytical data from said extracted data to interface with client applications configured for visualizing said analytical data,
- wherein said one or more database servers are further configured to convert said extracted data into one or more discrete-time data, to log said discrete-time data in said database and to make said discrete-time data available to said client applications as part of said analytical data; and
- wherein said one or more database servers are also configured to compute statistical indicators relating to said extracted data, to log said statistical indicators in said database and to make said statistical indicators available to said client applications as part of said analytical data.

15. The monitoring system as claimed in claim 1, implemented as a room occupant monitoring system in a hospital or a nursing home or a retirement home or a penal institution, said signal processing of said digital raw signal comprising detection of falls of a room occupant, in accordance with detection criteria.

16. The monitoring system as claimed in claim 3, comprising a wall skirting, said skirting having illumination devices integrated therein, said illumination devices being connected with and controllable by said relay.

17. The monitoring system as claimed claim 1, wherein the first electrode is patterned by insulating regions extending along straight axes so as to allow the pressure sensor to be cut to a desired shape with a reduced risk that the cutting will cause short-circuits between the first electrode and one of the second and shield electrodes.

18. The monitoring system as claimed in claim 1, wherein the first electrically insulating film and the second electrically insulating film are made of polyethylene terephthalate.

19. The monitoring system as claimed in claim 1, wherein the second electrode and the shield electrode are connected to ground, in such a way as to shield the first electrode, which is a signal electrode of the sensor, from external electromagnetic interference.

20. The monitoring system as claimed in claim 1, wherein the first electrode layer and the second electrode layer are made of aluminium, wherein the first electrically insulating film and the second electrically insulating film are made of polyethylene terephthalate, and wherein the second electrode and the shield electrode are connected to ground, in such a way as to shield the first electrode, which is a signal electrode of the sensor, from external electromagnetic interference.

* * * * *